United States Patent [19]

Mirell

[11] 4,124,804

[45] Nov. 7, 1978

[54] COMPTON SCATTER SCINTILLATION CAMERA SYSTEM

[76] Inventor: Stuart Mirell, 10816 Cushdon Ave., Los Angeles, Calif. 90064

[21] Appl. No.: 751,608

[22] Filed: Dec. 17, 1976

[51] Int. Cl.[2] .......................... G01N 23/00; G01T 1/20

[52] U.S. Cl. .............................. 250/358 R; 250/363 S; 250/445 T

[58] Field of Search ..................... 250/320, 321, 363 S, 250/445 T, 496, 358 R

[56] References Cited

U.S. PATENT DOCUMENTS 3,106,640 10/1963 Oldendorf ........................ 250/320 X

*Primary Examiner*—Davis L. Willis

*Attorney, Agent, or Firm*—Fulwider, Patton, Rieber, Lee & Utecht

[57] ABSTRACT

A method and apparatus for producing tomographic or cross-sectional radiographic images of a portion of a patient's anatomy, or of another object, by means of a planar-collimated gamma-ray source, from which the radiation is substantially confined to a single plane, and a conventional scintillation camera located to detect gamma radiation scattered from the object being examined, the scintillation camera including a collimator arranged to detect scattered radiation only from a direction perpendicular to the plane being examined.

6 Claims, 2 Drawing Figures

COMPTON SCATTER SCINTILLATION CAMERA SYSTEM

BACKGROUND OF THE INVENTION

This invention relates generally to radiography and, more particularly, to radiographic systems for producing tomographic, i.e., cross-sectional radiographic images.

Radiographic techniques using either x-rays or gamma rays are, of course, widely used in medicine. In general, most radiographic techniques depend upon the principle that radiation directed at some portion of a patient's anatomy will be blocked or attenuated to some degree depending upon the thickness, density and other characteristics of the irradiated substances. In conventional radiographic processes, x-rays are transmitted through a patient to a photographic film, where variations in thickness and density characteristics are recorded.

More recently, there has been much interest and development in the field of tomography, sometimes known as sectional radiography, which is the technique of making radiographs of plane sections of a body or object. In one tomographic technique, a pencil beam of x-rays is scanned through the patient along the plane to be examined, and a detector is utilized to monitor the intensity of the beam after it has traversed the patient. The x-ray source and detector assembly are slowly rotated about an axis substantially perpendicular to the plane of interest, and more radiographic data are collected at each incremental angular position. The data can then be correlated by computer, to generate a tomograpic image of the entire cross-section. Although this technique is highly effective, it requires relatively complex equipment to obtain and analyze the radiographic data, and to display the resultant tomographic images.

Accordingly, there is still a need in the field of tomography for a simplified technique for producing tomographic images, and it is to this end that the present invention is directed.

SUMMARY OF THE INVENTION

The present invention resides in a novel system for producing tomographic images using gamma rays and utilizing the Compton scattering principle. Briefly, and in general terms, the apparatus of the invention includes a planar-collimated gamma-ray source for irradiating a particular plane to be examined, this source being used in conjunction with a conventional scintillation camera collimated to detect only scattered radiation received along a direction normal to the plane being examined.

For the examination of portions of the human anatomy, it is contemplated that the planar-collimated source be annular in shape, and appropriately sized to encircle the portion of the body examined. The source material is chosen to have an energy level at which Compton scattering will be the predominant interaction between the gamma rays and the substance irradiated. In this well known process, the gamma rays are inelastically scattered by electrons in the irradiated substance, and the amount of scattered radiation increases with the density of the substance. Although the gamma rays are scattered in random directions, the scintillation camera, being collimated to receive only radiation from a direction normal to the plane being examined, will develop an image which accurately maps the variations in tissue density across the plane being examined.

The planar-collimated gamma-ray source may include a single localized source at its periphery, a plurality of localized sources spaced around the periphery, or a uniformly distributed source around the periphery. In any event, the collimated source may be rotated about an axis perpendicular to the plane of radiation, to distribute the effects of any nonuniformity of distribution of the radioactive material.

It will be appreciated from the foregoing that the present invention represents a significant advance in the field of radiographic tomography. In particular, it enables sectional images to be obtained relatively quickly and without the need for scanning techniques or complex data processing apparatus. Other aspects and advantages of the invention will become apparent from the following more detailed description, taken in conjunction with the accompanying drawings.

DETAILED DESCRIPTION

Figure 1:
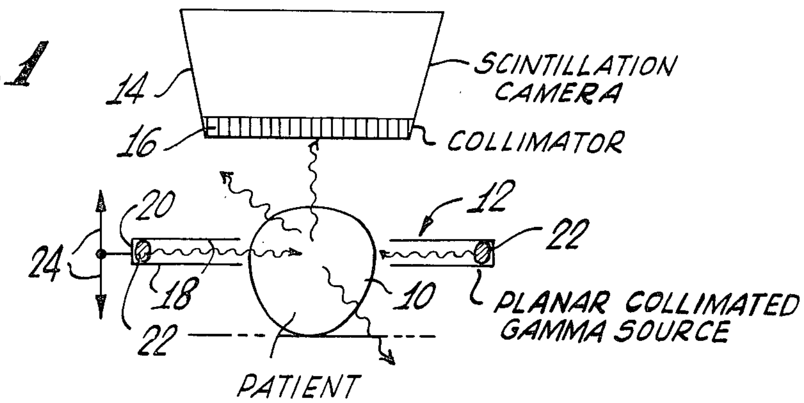
FIG. 1 is a diagrammatic cross-sectional view of the apparatus of the invention, including the planar-collimated gamma-ray source and scintillation camera.
Figure 2:
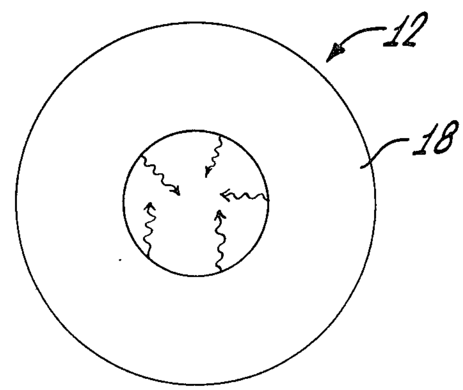
FIG. 2 is a plan view of the planar-collimated gamma-ray source.

As shown in the drawings for purposes of illustration, the present invention is embodied in novel apparatus for producing sectional or tomographic images. The invention is ideally suited for medical use, but is not limited to medical radiography.

In accordance with the invention, a plane section of a patient or object to be examined, indicated by reference numeral 10, is irradiated by means of an annular, planar-collimated gamma-ray source 12, and a scintillation camera 14 is positioned to detect scattered radiation from the irradiated plane, thereby recording variations in density across the plane. The gamma-ray source 12 is chosen to have an energy level which produces Compton scattering as the predominant interaction between the gamma rays and the substance being irradiated. This energy level is typically in the range of 0.1 to 1.0 million electron volts (MeV) for medical applications. As is well known, the Compton process is an inelastic scattering by electrons in the substance of incident high-energy photons or gamma rays. The scattered radiation provides an indication of the electron density of the substance being irradiated, and the electron density is, for all practical purposes, proportional to the mass density.

Since the scattering is random in direction, the scattered radiation that could be detected at any point spaced away from the irradiated plane section would be derived from secondary sources widely distributed over the plane section. However, if the scintillation camera is collimated to receive radiation only from a direction perpendicular to the plane being examined, as indicated at 16, then the radiation detected at any point in the plane of detection of the scintillation camera can only have been scattered from a corresponding point in the plane being examined.

The planar-collimated gamma-ray source 12 comprises a pair of flat annular plates 18, of lead or some other material which will act as a radiation shield, the plates being joined at their outer periphery by a circular rim 20, and being open at their inner periphery to allow the radiation to emerge inwardly from between the plates. Located between the plates is at least one portion 22 of a gamma-ray emitting radioactive material. There may be a single such portion located at one point in the outer periphery of the collimated source 12, or a plurality of uniformly spaced portions, or a uniformly distributed portion of the material. In any event, the assembly comprising the annular plates 18, the rim 20, and the radioactive material 22 may be rotated during the exposure of the patient, in order to distribute any nonuniformities of the radiation pattern arising from the localized nature of the radioactive material. Since the radiation is principally planar, there will be no direct irradiation of parts of the body other than in the plane section being examined. The collimated source 12 may be moved perpendicularly to the irradiated plane, as shown by the arrows 24, to examine other parallel plane sections of the patient's anatomy.

Scintillation cameras of the type utilized in this invention are well known in nuclear medicine. This type of camera is conventionally used to produce an image of the distribution of radioisotopes injected into a patient. It is sometimes referred to as an Anger camera or a gamma camera. The collimator used with the scintillation camera is also of conventional design. Collimator designs for scintillation cameras are shown, for example, in U.S. Pat. No. 3,852,598 issued in the name Larsson. The scintillation camera is usually constructed in the form of an array of scintillation detectors from which corresponding electrical pulses are produced on the detection of each incident gamma ray. The pulses can be selectively filtered in accordance with their amplitude or height, and are then displayed in the form of a planar image. The pulse height filtration is performed by an electronic "window" which admits only a narrow range of pulses from a broad spectrum. In its conventional use, the window on the scintillation camera is centered at a level $E_o$ corresponding to the energy of gamma rays emitted from an injected radioisotope.

The window in the scintillation camera as utilized in this invention is centered at an energy E which is the diminished energy of a gamma ray of initial energy $E_o$ subsequent to a 90° scatter. The relationship between E and $E_o$ is given by $1/E = 1/E_o + 1/511$, where the energies are expressed in KeV.

One advantage of the present invention is that the conventional scintillation camera 14 may be used essentially without modification to obtain tomographic images. A less obvious advantage is that the planar-collimated gamma-ray source requires considerably less radioactive material than is needed by pencil-beam systems for producing tomographic images; in fact, less than 1% of the radioactive material of pencil-beam systems.

The strict use of the term "gamma ray" implies a photon resulting from an electromagnetic transition within an atomic nucleus. Such transitions often produce photons far more energetic than photons generated in other physical processes. As a consequence, common usage of "gamma ray" frequently connotes an energetic photon irrespective of its physical origin. The radiation source in the described invention must necessarily provide photons which interact significantly by Compton scattering. In this regard, the physical origin of the photon source is not directly relevant to the imaging process of this invention. The "gamma ray" source may, in fact, be a source of annihilation photons, bremsstrahlung radiation, or x-radiation as well as photons emitted from nuclear transitions.

It will be appreciated from the foregoing that the present invention represents a significant advance in the field of sectional radiography. In particular, it provides a simple technique for producing tomographic images without the use of scanning beams or complex data-processing techniques. It will also be appreciated that, although the invention has been described in relation to a particular embodiment illustrated herein by way of example, various modifications may be made without departing from the spirit and scope of the invention. Accordingly, the invention is not to be limited except as by the appended claims.

I claim:

1. A sectional radiographic imaging system comprising:
- a planar-collimated source of gamma radiation located to provide essentially simultaneous irradiation of an entire plane of an object to be examined; and
- a scintillation camera located to detect scattered radiation across a plane substantially parallel to the plane being examined, and including collimation means arranged to restrict the detected radiation to scattered rays having trajectories substantially normal to the two planes, whereby the gamma radiation is confined to the plane being examined and gives rise to Compton-scattered radiation emanating from that plane, the scattered rays normal to the two planes being detected in said scintillation camera to provide an accurate and essentially instantaneous image of the variation in density across the entire plane being examined.

2. A system as set forth in claim 1, wherein said planar-collimated source of gamma radiation comprises a pair of relatively closely spaced shielding plates of annular shape, and a portion of radioactive material positioned between said plates and near their outer periphery, whereby the radiation emitted between the plates is essentially confined to a plane inside the annulus of the plates.

3. A method of producing tomographic images comprising the steps of:
- irradiation essentially simultaneously an entire plane of an object to be examined by means of a planar-collimated gamma-ray source;
- detecting Compton-scattered radiation received at a position sensitive detector plane in a direction substantially normal to the detector plane and the plane being examined, said detecting step being performed essentially simultaneously over the entire detector plane; and
- generating an image from the detected scattered radiation, corresponding to physical characteristics across the plane being examined.

4. A method as set forth in claim 3, and further including the step of rotating the planar-collimated gamma-ray source about an axis substantially perpendicular to the plane being examined, to minimize the effect of any nonuniformity in the planar-collimated gamma-ray source.

5. A method as set forth in claim 3, and further including the step of moving the planar-collimated gamma-ray source perpendicularly to the plane being examined, to allow examination of different planes in the same object.

6. For use in a sectional radiographic imaging system, a planar-collimated source of gamma radiation, comprising:

a pair of relatively closely spaced shielding plates of essentially annular shape, locatable to surround an object to be examined; and a portion of radioactive material positioned between said plates and near their outer periphery, whereby the radiation emitted between said plates simultaneously irradiates an entire plane section of the object, is Compton-scattered therefrom, and is detectable in a plane parallel to the one being irradiated, to provide an image of density variations across the irradiated plane.

* * * * *

UNITED STATES PATENT AND TRADEMARK OFFICE
CERTIFICATE OF CORRECTION

PATENT NO. : 4,124,804

DATED : November 7, 1978

INVENTOR(S) : STUART MIRELL

It is certified that error appears in the above-identified patent and that said Letters Patent are hereby corrected as shown below:

Column 1, line 55, after "body" insert therefor --being--.

Column 4, line 43, "irradiation" should be --irradiating--.

Signed and Sealed this

*First* Day of *April 1980*

[SEAL]

*Attest:*

SIDNEY A. DIAMOND

*Attesting Officer* *Commissioner of Patents and Trademarks*